United States Patent
Leppard et al.

(10) Patent No.: US 6,495,622 B1
(45) Date of Patent: Dec. 17, 2002

(54) DIMERIC LIGHT STABILIZERS FOR POLYOLEFINES AND POLYOLEFINE COPOLYMERS

(75) Inventors: David George Leppard, Marly (CH); Vien Van Toan, Rheinfelden (CH); Roland A. E. Winter, Armonk, NY (US); Michela Bonora, Bologna (IT)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/722,975

(22) Filed: Nov. 27, 2000

Related U.S. Application Data
(60) Provisional application No. 60/167,759, filed on Nov. 29, 1999.

(51) Int. Cl.[7] .............................. C07F 7/08; C07F 7/18; C08K 5/132

(52) U.S. Cl. ....................... 524/335; 568/332; 568/333; 556/436

(58) Field of Search ................... 524/338, 91, 335; 568/333, 332; 548/260, 261; 556/436

(56) References Cited

U.S. PATENT DOCUMENTS

| | | | |
|---|---|---|---|
| 3,580,927 A | 5/1971 | Wear | ........... 524/335 |
| 4,973,702 A | * 11/1990 | Rody et al. | |
| 5,756,793 A | * 5/1998 | Valet et al. | |
| 6,117,997 A | 9/2000 | Bulliard et al. | ........... 544/216 |

FOREIGN PATENT DOCUMENTS

| | | |
|---|---|---|
| CS | 174557 | 10/1978 |
| DE | 2350180 | 4/1975 |
| JP | 05320619 | 5/1993 |
| WO | 98/03489 | 1/1998 |

OTHER PUBLICATIONS

Derwent Abstr. 1975–29228W for DE 2350180 (1975).
Derwent Abstr. 93–320619 for JP 05320619 (1993).
Derwent Abstr. 94–115390/14 for JP 06065541 (1992).
Derwent Abstr. 91–087974/13 for DE 3930516 (1989).

* cited by examiner

*Primary Examiner*—Peter Szekely
(74) *Attorney, Agent, or Firm*—Tyler A. Stevenson

(57) ABSTRACT

Compositions comprising
  A) a polyolefin or polyolefin copolymer, and
  B) a compound of the formula I

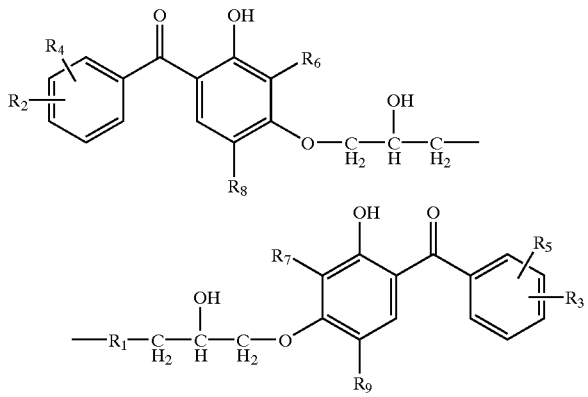

wherein
  $R_1$ is O or O—X—O;
  $R_2$, $R_3$, $R_4$ and $R_5$ independently are hydrogen, halogen, $C_1$–$C_8$alkyl, $C_1$–$C_8$alkoxy, $SR_{10}$, $SO_2R_{10}$, phenyl, $CF_3$, $COOR_{11}$; and wherein $R_2$ and $R_3$ also may be OH;
  $R_6$ and $R_7$ are H or $C_1$–$C_8$alkyl;
  $R_8$ and $R_9$ are H, $C_1$–$C_8$alkyl or allyl;
  $R_{10}$ is phenyl or $C_1$–$C_{12}$alkyl;
  $R_{11}$ is $C_1$–$C_8$alkyl; $C_3$–$C_{50}$alkylene interrupted by one or more O; cyclohexyl; benzyl; allyl;
  X is $C_2$–$C_{18}$alkylene; $C_3$–$C_{12}$hydroxyalkylene; or a group selected from those of the formulae

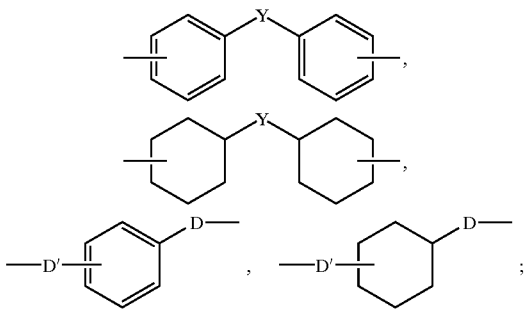

where D and D' independently are a direct bond or $C_1$–$C_3$alkylene; and
  Y is O, S, $SO_2$, or $C_1$–$C_3$alkylene, e.g. polyethylene films, are well stabilized against the effects of light, oxygen and heat. Some novel compounds of component B are valuable stabilizers for organic material against damage by light, oxygen and/or heat.

13 Claims, No Drawings

DIMERIC LIGHT STABILIZERS FOR POLYOLEFINES AND POLYOLEFINE COPOLYMERS

This application claims the benefit under 35 U.S.C. 119(e) of U.S. Provisional Application No. 60/167,759, Filed Nov. 29, 1999.

The invention relates to novel compositions comprising a polyolefin or polyolefin copolymer, and a dimeric 2-hydroxybenzophenone as stabilizer against damage by light, oxygen and/or heat; and further to novel compounds of the 2-hydroxybenzophenone class useful as stabilizers for organic material, and a corresponding process of stabilizing.

A considerable number of organic compounds containing a group 2-hydroxybenzophenone are known to be efficient light stabilizers for protecting organic materials against deleterious effects of (ultraviolet) light, oxygen and heat. Some dimeric benzophenones known from U.S. Pat. No. 3,580,927 have been recommended for the stabilization of certain polyesters.

Some compounds have now been found showing surprisingly good properties for the stabilization of polyolefines or polyolefin copolymers against harmful effects of actinic light, oxygen and heat.

Thus, present invention pertains to a composition comprising
A) a polyolefin or polyolefin copolymer, and
B) as stabilizer against damage by light, oxygen and/or heat, a compound of the formula I

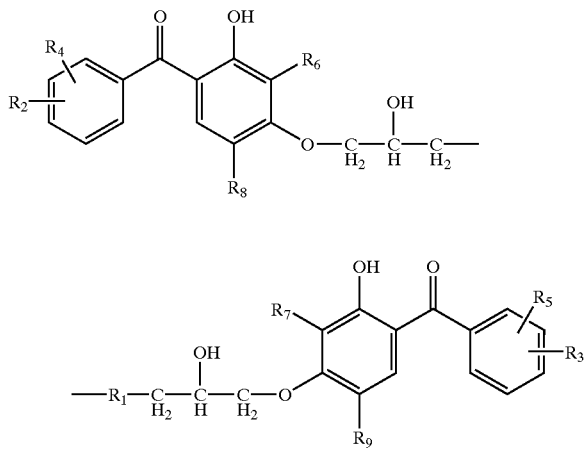

wherein
$R_1$ is O or O—X—O;
$R_2$, $R_3$, $R_4$ and $R_5$ independently are hydrogen, halogen, $C_1$–$C_8$alkyl, $C_1$–$C_8$alkoxy, $SR_{10}$, $SO_2R_{10}$, phenyl, $CF_3$, $COOR_{11}$; and wherein $R_2$ and $R_3$ also may be OH;
$R_6$ and $R_7$ are H or $C_1$–$C_8$alkyl;
$R_8$ and $R_9$ are H, $C_1$–$C_8$alkyl or allyl;
$R_{10}$ is phenyl or $C_1$–$C_{12}$alkyl;
$R_{11}$ is $C_1$–$C_8$alkyl; $C_3$–$C_{50}$alkylene interrupted by one or more O; cyclohexyl; benzyl; allyl;
X is $C_2$–$C_{18}$alkylene; $C_3$–$C_{12}$hydroxyalkylene; or a group selected from those of the formulae

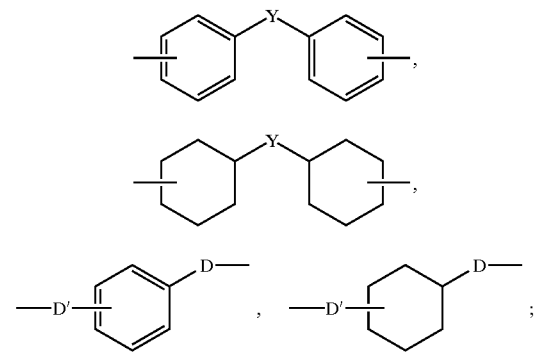

where D and D' independently are a direct bond or $C_1$–$C_3$alkylene; and Y is O, S, $SO_2$, or $C_1$–$C_3$alkylene.

Alkylene, cycloalkylene or alkenylene residues may be bonded on different carbon atoms or on the same carbon atom thus embracing alkylidene, cycloalkylidene and alkenylidene, respectively.

All residues, where appropriate, may be straight chain or branched unless otherwise indicated. Alkyl or alkylene interrupted by a spacer such as oxygen may be interrupted by one or more spacers as long as no linkages of the type O—O etc. occur.

Halogen is F, Cl, Br or I; preferably chloro or fluoro, especially chloro.

The compounds of formula I can be pure or mixtures of compounds.

$R_1$, $R_2$, $R_3$, $R_4$, $R_5$, $R_6$, $R_7$, $R_8$, $R_9$, $R_{10}$, $R_{11}$, as alkyl are, within the definitions given, for example methyl, ethyl, propyl such as n- or isopropyl, butyl such as n-, iso-, sec- and tert-butyl, pentyl, hexyl, heptyl, octyl, nonyl, decyl, undecyl, dodecyl, tridecyl, tetradecyl, pentadecyl, hexadecyl, heptadecyl or octadecyl. Alkoxy is O-alkyl. X, D and Y as alkylene are, within the definitions given, for example methylene, 1,2-ethylene, 1,1-ethylene, 1,3-propylene, 1,2-propylene, 1,1-propylene, 2,2-propylene, 1,4-butylene, 1,3-butylene, 1,2-butylene, 1,1-butylene, 2,2-butylene, 2,3-butylene, or —$C_5H_{10}$—, —$C_6H_{12}$—, $C_7H_{14}$, —$C_8H_{16}$—, —$C_9H_{18}$—, —$C_{10}H_{20}$—, —$C_{11}H_{22}$—, —$C_{12}H_{24}$—, —$C_{13}H_{26}$—, —$C_{14}H_{28}$—, —$C_{15}H_{30}$—, —$C_{16}H_{32}$—, —$C_{17}H_{34}$—, —$C_8H_{36}$—. D and Y are especially preferred as methylene. X as hydroxyalkylene is alkylene substituted by one or more OH and includes, for example, groups of the formulae $CH_2CH(OH)CH_2$, $CH_2$—$C(CH_2OH)_2$—$CH_2$.

Preferred in the compositions of the invention are compounds corresponding to the formula

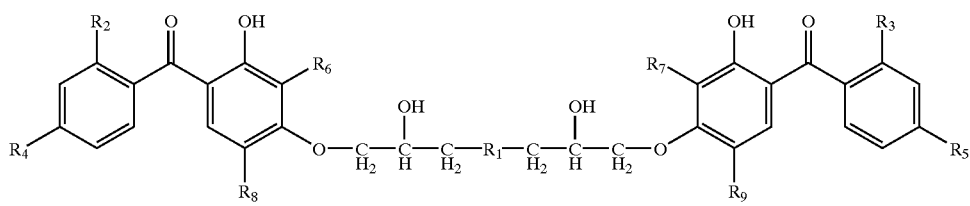

wherein
R₁ is O or O—X—O;
R₂ and R₃ are hydrogen, Cl, $C_1$–$C_8$alkyl, $C_1$–$C_4$alkoxy, OH;
R₄ and R₅ are hydrogen, Cl, F, $C_1$–$C_8$alkyl, $C_1$–$C_4$alkoxy, SR₁₀, SO₂R₁₀, phenyl, CF₃, COOR₁₁;
X is $C_2$–$C_{12}$alkylene; phenylene, or a group selected from those of the formulae

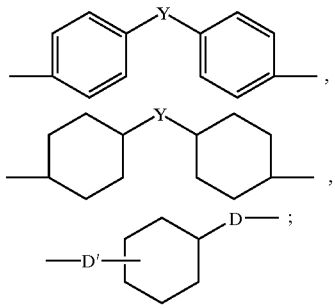

where D and D' independently are a direct bond or are methylene; and
Y is O, S, SO₂, or $C_1$–$C_3$alkylene.
More preferred is a compound of the formula I wherein
R₁ is O or O—X—O;
R₂ and R₃ are hydrogen, Cl, $C_1$–$C_8$alkyl, $C_1$–$C_4$alkoxy, OH;
R₄ and R₅ are hydrogen, Cl, $C_1$–$C_8$alkyl, $C_{11}$–$C_4$alkoxy, SR₁₀, SO₂R₁₀, phenyl,
X is $C_2$–$C_{12}$alkylene; cyclohexylene, or a group selected from those of the formulae

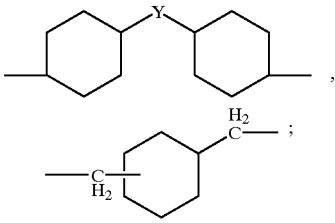

where Y is O, S, SO₂, methylene or —C(CH₃)₂—.
Most preferred is a compound of the formula I wherein
R₁ is O—X—O,
R₂ and R₃ are hydrogen, Cl;
R₄ and R₅ are hydrogen, Cl, $C_1$–$C_8$alkyl, $C_1$–$C_4$alkoxy, SR₁₀, SO₂R₁₀, phenyl, CF₃;
R₆, R₇, R₈ and R₉ are each H,
X is $C_2$–$C_{12}$alkylene; cyclohexylene, or a group selected from those of the formulae

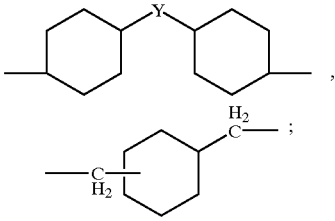

where Y is methylene or —C(CH₃)₂—; especially wherein
R₂ and R₃ are hydrogen;
R₄ and R₅ are hydrogen or Cl;
R₆, R₇, R₈ and R₉ each are hydrogen.

X is most preferred as $C_8$–$C_{18}$alkylene, usually unbranched; especially preferred is X selected from the group consisting of (CH₂)₈; (CH₂)₁₀; (CH₂)₁₂; (CH₂)₁₈.

Of special importance as component A are polyolefines or polyolefin copolymers as described in sections 1–3 below, especially in the form of films, ribbons, tapes, fibers or fabrics, e.g. for agricultural or packaging uses. Examples for specific uses include:

| | |
|---|---|
| Polypropylene non-woven fabric for agricultural applications, e.g. shade cloth | Polyolefin films with an antifog agent |
| Polyolefin films with an antistatic agent | Polyolefin films with IR thermal fillers such as hydrotalcites, e.g. DHT4A |
| Polypropylene tape or slit film Polyethylene non-woven fabrics | Polypropylene non-woven fabrics Polyethylene greenhouse films, optionally containing hindered amine light stabilizers and/or hydrotalcites |
| Flame-resistant polypropylene fiber Flame-resistant polethylene film | Polyolefin foodpackaging film |

The polyolefin or polyoiefin copolymer of present component A is, for example, selected from the following polymers:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or τ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, Ia and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

Some compounds of the formula I are novel compounds. Thus, another object of the invention are compounds of the formula Ia

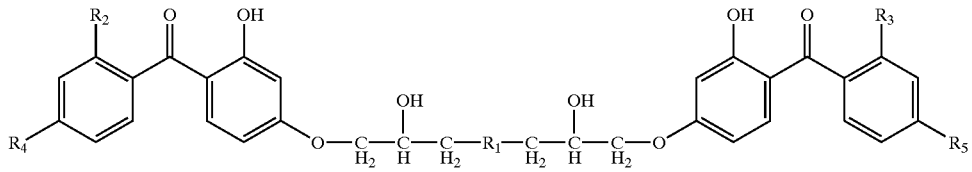

wherein
$R_1$ is O or O—X—O;
$R_2$, $R_3$, $R_4$ and $R_5$ independently are hydrogen, halogen, $C_1$–$C_8$alkyl, $C_1$–$C_8$alkoxy, $SR_{10}$, $SO_2R_{10}$, phenyl, $CF_3$, $COOR_{11}$; and wherein $R_2$ and $R_3$ also may be OH;
$R_{10}$ is phenyl or $C_1$–$C_{12}$alkyl;
$R_{11}$ is $C_1$–$C_8$alkyl; $C_3$–$C_{50}$alkylene interrupted by one or more O; cyclohexyl; benzyl; allyl;
X is $C_6$–$C_{18}$alkylene; $C_3$–$C_{12}$hydroxyalkylene; or a group selected from those of the formulae

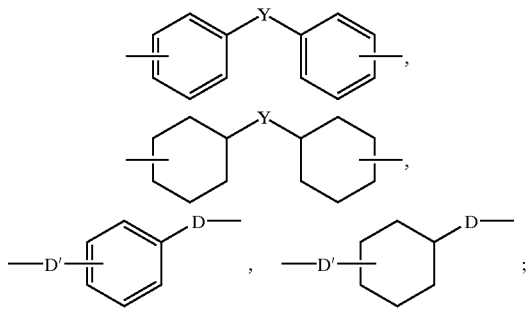

where D and D' independently are a direct bond or $C_1$–$C_3$alkylene; and
Y is O, S, $SO_2$.

Preferred compounds of the formula Ia are, within the above definition, basically as defined for compounds of the formula I.

The preparation of compounds of the formula I or Ia can follow methods known in the art (e.g. U.S. Pat. No. 3,580,927); some analogous reactions are described, for example, in EP-A-434608 and specifically in example 1 of this publication.

Preferably, 2 equivalents of a benzophenone educt of the formula E1

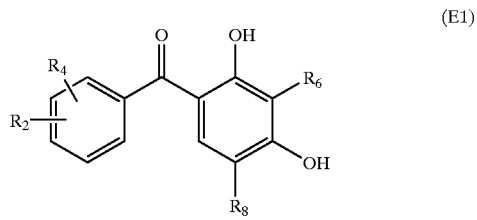

are reacted with a diglycidyl ether of the formula E2

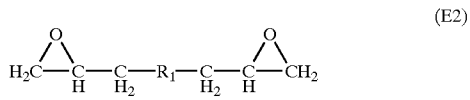

with formation of the compound of formula I.

Alternatively, the synthesis can starting with 2 equivalents of the formula E3 (conveniently to be obtained from the reaction of educt E1 with epichlorohydrine)

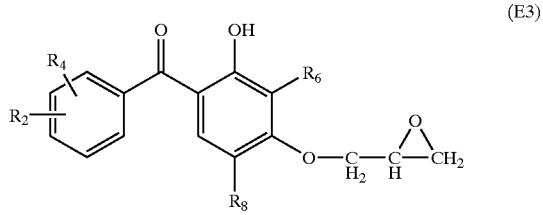

reacted with 1 equivalent of dialcohol HO—X—OH.

Asymmetric products, wherein $R_2$, $R_4$, $R_6$, $R_8$ are different from $R_3$, $R_5$, $R_7$, $R_9$, are obtained using a corresponding mixture of educts E1 or E3. Preferred are symmetric products, wherein $R_2$ equals $R_3$; $R_4$ equals $R_5$; $R_6$ equals $R_7$; and $R_8$ equals $R_9$. Ring opening of the epoxides usually follows methods known in the art and may be acid catalyzed.

The novel compounds of present invention can be employed with advantage for stabilizing organic material against the damaging effect of light, oxygen and/or heat. They are notable for high substrate compatibility and good persistence in the substrate.

Examples of materials to be stabilized with compounds of the formula Ia in accordance with the invention are given in U.S. Pat. No. 6,117,997, column 11, line 62, until column 15, line 43; these passages of U.S. Pat. No. 6,117,997 are hereby incorporated by reference.-

The invention therefore also provides compositions comprising

A) an organic material which is sensitive to oxidative, thermal and/or actinic degradation, and B) at least one compound of the formula Ia, and provides for the use of compounds of the formula I for stabilizing organic material against oxidative, thermal or actinic degradation.

Effects of degradation inter alia may be discoloration, molecular breakdown or buildup. Thus, the invention likewise embraces a method of stabilizing organic material against thermal, oxidative and/or actinic breakdown/buildup, which comprises applying or adding at least one compound of the formula Ia to this material.

In general, the compounds of the formula I or Ia are added to the material to be stabilized in amounts of from 0.01 to 10%, preferably from 0.01 to 5%, in particular from 0.01 to 2% (based on the weight of the material to be stabilized).

Particular preference is given to the use in amounts of from 0.05 to 1.5%, especially from 0.1 to 0.5% by weight.

Of particular interest is the use of the novel compounds of the formula Ia as stabilizers in synthetic organic polymers, especially thermoplastic polymers, and corresponding compositions, in film forming binders for coatings and in reprographic material.

The organic materials to be protected are preferably natural, semisynthetic or, preferably, synthetic organic materials. Particular preference is given to synthetic organic polymers or mixtures of such polymers, especially thermoplastic polymers such as polyolefins, especially polyethylene and polypropylene (PP), and coating compositions.

In addition to the compounds of the formula I or Ia, the novel compositions may as additional component C comprise one or more conventional additives such as, for example, those indicated below.

1. Antioxidants 1.1. Alkylated monophenols, for example 2,6-di-tert-butyl-4-methylphenol, 2-tert-butyl-4,6-di-methylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethyl-phenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl) phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octade-cyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl)disulfide.

1.6. Alkylidenebisphenols, for example 2,2'-methylenebis (6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis-(2,6-di-tert-butylphenol), 4,4'-methylenebis (6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy-2-methylphenyl)pentane.

1.7. O—, N— and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxy-benzyl)sulfide, isooctyl-3,5-di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, didodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis (octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris-(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris-(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3.5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)ox-amide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxy-phenylpropionyl) trimethylenediamide, N,N'-bis(3,5-di-tert-butyl-4-hydroxyphenyipropionyl)-hydrazide, N,N'-bis[2-(3-[3,5-di-tert-butyl-4-hydroxyphenyl]propionyloxy)ethyl]oxamide (Nau-gard® XL-1 supplied by Uniroyal).

1.18. Ascorbic acid (vitamin C)

1.19. Aminic antioxidants, for example N,N'-diisopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenlenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)-propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- und dialkylated tert-butyldiphenylamines, 2,3-dihydro-3,3-dimethyl-4H-1,4-benzothiazine, phenothiazine, a mixture of mono- und dialkylated tert-butyl/-tert-octylphenothiazines, a mixture of mono- und dialkylated tert-octyl-phenothiazines, N-allylphenothiazin, N,N,N',N'-tetraphenyl-1,4-diaminobut-2-ene, N,N-bis(2,2,6,6-tetramethyl-piperid-4-yl-hexamethylenediamine, bis(2,2,6, 6-tetramethylpiperid-4-yl)sebacate, 2,2,6,6-tetramethylpiperidin-4-one, 2,2,6,6-tetramethylpiperidin-4-ol.

2. UV Absorbers and Light Stabilisers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl) benzotriazole, 2-(2'-hydroxy-4'-octyloxyphenyl) benzotriazole, 2-(3',5'-di-tert-amyl-2'-hydroxyphenyl) benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl) phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonyl-ethyl)phenyl) benzotriazole, 2-(3'-tert-butyl-5'-[2-(2-ethylhexyloxy) carbonylethyl]-2'-hydroxy-phenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl) phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$—]$_2$ where R=3'-tert-butyl-4'-hydroxy-5'-2H-benzotriazol-2-ylphenyl, [2-2'-hydroxy-3'-(α,α-dimethylbenzyl)-5'-(1,1,3,3-tetramethylbutyl)-phenyl]-benzotriazole; 2-[2'-hydroxy-3'-(1,1,3,3-tetramethylbutyl)-5'-(α,α-dimethylbenzyl)-phenyl]benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis (4-tert-butylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-β-methoxy-cinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyidithiocarbamate, nickel salts of the monoalkyl esters, e.g. the methyl or ethyl ester, of 4-hydroxy-3,5-di-tertbutylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)-malonate, 3-n-octyl-7,7,9,9-tetramethyl-1,3,8-triazaspiro[4.5]decan-2,4-dione, bis(1-octyloxy-2,2,6,6-tetramethylpiperidyl) sebacate, bis(1-octyloxy-2,2,6,6-tetramethylpiperidyl) succinate, linear or cyclic condensates of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)-ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl) pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis (2,2,6,6-tetramethyl-4-piperidyl)hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3,8-diaza-4-oxo-spiro [4,5]decane, a reaction product of 7,7,9,9-tetramethyl-2-cycloundecyl-1-oxa-3,8-diaza-4-oxospiro [4,5]decane und epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl) hexamethylenediamine, diester of 4-methoxy-methylenemalonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis (2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy) phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy) phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenyihydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz-[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-12-methyl-dibenz[d,g]-1,3,2-dioxaphosphocin, 2,2',2"-nitrilo[triethyltris(3,3',5,5'-tetra-tert-butyl-1,1'-biphenyl-2,2'-diyl)phosphite], 2-ethylhexyl (3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

Especially preferred are the following phosphites:

Tris(2,4-di-tert-butylphenyl) phosphite (Irgafos® 168, Ciba-Geigy), tris(nonylphenyl) phosphite,

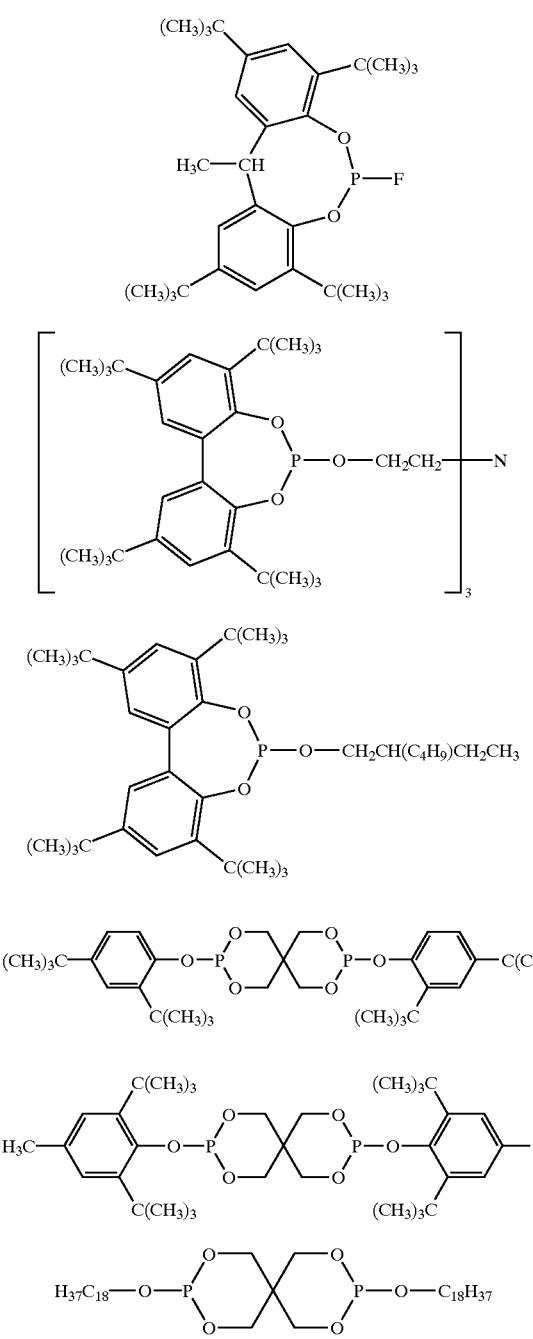

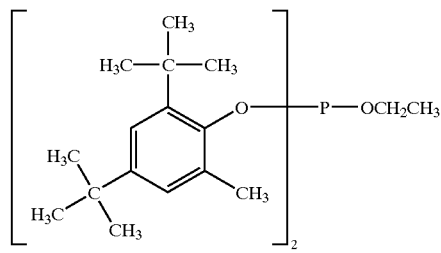

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridcyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-dialkylhydroxyl-amine derived from hydrogenated tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or zink pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers). Especially preferred are 1,3:2,4-bis(3',4'-dimethylbenzylidene)sorbitol, 1,3:2,4-di(paramethyidibenzylidene)sorbitol, und 1,3:2,4-di(benzylidene)sorbitol.

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839 or EP-A-0591102 or 3-[4-(2-acetoxyethoxy)-phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, 3-(2,3-di-methylphenyl)-5,7-di-tert-butyl-benzofuran-2-one.

The conventional additives are judiciously employed in amounts of 0.1–10% by weight, for example 0.2–5% by weight, based on the material to be stabilized.

Costabilizers optionally to be added to the stabilizer mixture of the invention are preferably further light stabilizers, for instance those of the 2-hydroxyphenyl-benztriazole, 2-hydroxyphenyl-triazine or oxalanilide classes or further benzophenones, e.g. as described in EP-A-453396, EP-A-434608, U.S. Pat. No. 5,298,067, WO 94/18278, GB-A-2297091 and WO 96/28431, and/or hindered amines derived from 2,2,6,6-tetraalkylpiperidine containing at least one group of the formula

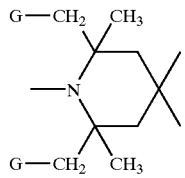

in which G is hydrogen or methyl, especially hydrogen; examples of tetraalkylpiperidine derivatives which can be used as costabilizers with mixtures of the invention are given in EP-A-356 677, pages 3–17, sections a) to f). These sections of this EP-A are regarded as part of the present description. Examples of such light stabilizers are listed above in sections 2.1, 2.2, 2.6, 2.7 and 2.8.

Polyolefines or polyolefin copolymers stabilized according to present invention preferably contain a processing stabilizer, e.g. a phenolic antioxidant as listed above in section 1 and/or an organic phosph(on)ite as listed above in section 4, often combined with a basic costabilizer (section 10) such as calcium stearate.

Incorporation into the materials to be stabilized can be effected, for example, by mixing in or applying the compounds of the formula I or Ia and, if desired, further additives by the methods which are customary in the art. Where polymers are involved, especially synthetic polymers, incorporation can take place prior to or during the shaping operation, or by applying the dissolved or dispersed compound to the polymer, with or without subsequent evaporation of the solvent. In the case of elastomers, these can also be stabilized as latices. A further possibility for incorporating the compounds of the formula I or Ia into polymers is to add them before, during or directly after the polymerization of the corresponding monomers or prior to crosslinking. In this context the compound of the formula can be added as it is or else in encapsulated form (for example in waxes, oils or polymers). In the case of addition prior to or during the polymerization, the compounds of the formula I or Ia can also act as a regulator of the chain length of the polymers (chain terminator).

The compounds of the formula I or Ia can also be added in the form of a masterbatch containing said compound in a concentration, for example, of from 2.5 to 25% by weight to the polymers that are to be stabilized.

The compounds of the formula I or Ia can judiciously be incorporated by the following methods:

- as emulsion or dispersion (e.g. to latices or emulsion polymers),
- as a dry mixture during the mixing in of additional components or polymer mixtures,
- by direct introduction into the processing apparatus (e.g. extruders, internal mixers, etc),
- as solution or melt.

Novel polymer compositions can be employed in various forms and/or processed to give various products, for example as (to give) films, fibres, tapes, moulding compositions, profiles, or as binders for coating materials, adhesives or putties.

Likewise of particular interest is the use of the novel mixtures comprising compounds of the formula Ia as stabilizers for coatings, for example for paints. The invention therefore also relates to compositions containing (A) is a film-forming binder for coatings and (B) a novel compound of the formula Ia.

Methods of using a novel compound of the formula Ia as stabilizer for coatings are as described in U.S. Pat. No. 6,117,997, column 26, line 59, until column 32, line 21, for stabilizers of formula I of (component B) of U.S. Pat. No. 6,117,997; these passages of U.S. Pat. No. 6,117,997 are hereby incorporated by reference.

The examples below illustrate the invention further. All parts or percentages, in the examples as in the remainder of the description and in the claims, are by weight, unless stated otherwise. Room temperature denotes a temperature in the range 20–30° C., unless stated otherwise. Data given for elemental analysis are in % by weight calculated (cal) or experimentally measured (exp) for the elements C, H and N. In the examples, the following abbreviations are used:

% w/w percent by weight;
% w/v percent weight by volume; x % (w/v) stands for x g solid dissolved in 100 ml liquid;
m.p. melting point or range;
PP polypropylene;
LDPE low density polyethylene;
DSC differential scan calorimetry;
NMR nuclear magnetic resonance (of $^1$H, if not otherwise indicated).

A: PREPARATION EXAMPLES

Example A1

1,8-di-[2-Hydroxy-3-(3-hydroxy-4-benzoylphenoxy)-propoxy]-octane

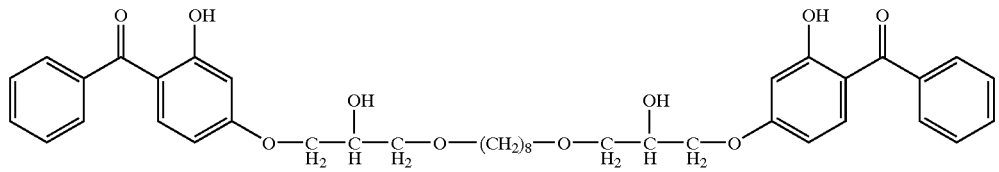

1,3-Di-hydroxybenzophenone (47.1 g), 1,8-octanediol-diglycidyl ether (25.8 g) and ethyl-triphenylphosphonium bromide (3.7 g) are heated in 150 ml refluxing xylene for 18 hrs. A further 0.19 g ethyl-triphenylphosphonium bromide is added and heating continued for 28 hours. The reaction mixture is filtered hot and the solution evaporated under reduced pressure to give 79 g of an orange oil. This is purified by column chromatography over 2 kg silica gel using hexane/ethylacetate 1:1 as eluant giving 49.7 g of the desired compound as a yellow powder, m.p. 74° C.

Example A2

1,6-di-[2-Hydroxy-3-(3-hydroxy-4-benzoylphenoxy)-propoxy]-hexane

Proceeding as described in example A1 but using the equivalent amount of 1,6-hexanediol-diglycidyl ether instead of 1,8-octanediol-diglycidyl ether yields the title product as a highly viscous liquid.

Example A3

Proceeding as described in example A1 but using the equivalent amount of the diol diglycidylether of the formula

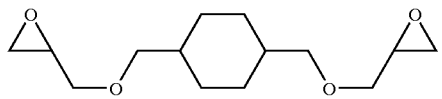

yields the compound

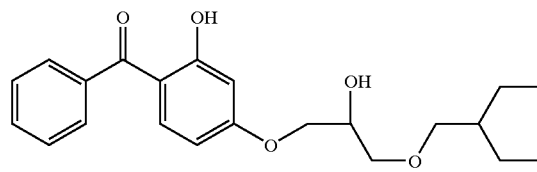

A3

Example A4

Proceeding as described in example A2 but using the equivalent amount of 1,3-Di-hydroxy-4-tert.amyl-benzophenone instead of 1,3-Di-hydroxybenzophenone yields the compound

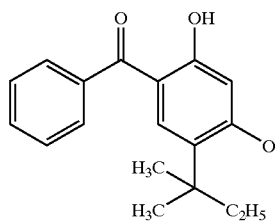

of m.p. 85–90° C.

B: Application Example

Example B1

Stabilization of Polyethylene Films

In order to prepare thin LDPE films and to evaluate the spectral features imparted by the additive and its persistency, the compound of example A1 or A2 is mixed with LDPE pellets (Riblene® FF 29, supplied by Enichem, Milano, Italy), characterized by a density of 0.921 g/cm$^3$ and a melt flow index (190° C./2.16 Kg) of 0.6 in a turbo mixer, at 0.6% by weight and at 0.8% by weight additive concentrations of example A1, or at 0.8% by weight and at 1.0% by weight additive concentrations of example A2, each based on the weight of the LDPE.

The mixtures are extruded at a maximum temperature of 200° C. in a OMC® twin-screw extruder. The granules so obtained are blown in a lab scale format blow-extruder at a maximum temperature of 210° C. to give films 150 μm thick. UV-Vis spectra are recorded in the range 200–800 nm for each film by means of a Perkin-Elmer lambda 20® spectrophotometer, equipped with a RSA-PE-20 Labsphere integrating sphere.

The above mentioned compounds display strong absorption in the range 280–360 nm. In particular, transmittance values below 5% are detected as follows:

compound of example A1: for the 0.6% concentration in the range 290–340 nm, and for the 0.8% concentration in the range 290–350 nm;

compound of example A2: for the 0.8% concentration in the range 290–350 nm, and for the 1.0% concentration in the range 290–360 nm.

Films are also exposed in a forced circulating air oven at 60° C., in order to evaluate the persistency of the additive in the film. UV-Vis spectra are periodically performed on the exposed samples and the maximum absorbance value is taken as a measure of the permanency of the additive, due to heat ageing of the films.

Result: The original transmittance values below 5% are kept after a total of 3000 hours oven ageing for both compounds.

Films are also exposed in a Atlas Xenon-Arc-Weather-O-Meter® Ci65A, at 63° C. black panel temperature and 0.35 kW/cm$^2$ irradiation at 340 nm, in order to evaluate the

A4

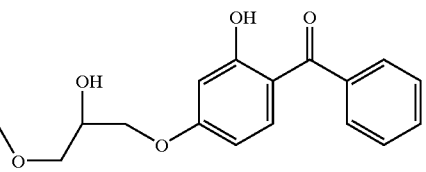

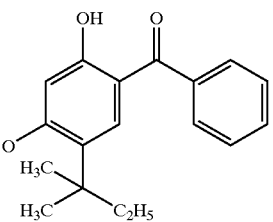

photostability of the additive in the film. UV-Vis spectra are periodically performed on the exposed samples and the maximum absorbance value is taken as a measure of the stability of the additive during exposure of the film to UV light. The resultant transmittance is given in the following tables.

TABLE 1

Transmittance of films stabilized with compound of example A1 after 1050 hours

| Concentration of stabilizer | Transmittance | in Spectral Range |
|---|---|---|
| 0.8% | below 5% | 290–350 nm |
| 0.6% | below 8% | 290–340 nm. |

TABLE 2

Transmittance of films stabilized with compound of example A2 after 1080 hours

| Concentration of stabilizer | Transmittance | in Spectral Range |
|---|---|---|
| 0.8% | below 10% | 290–340 nm |
| 1.0% | below 5% | 290–350 nm. |

The results show a good photostability and persistency of the stabilizers of the invention in the film.

What is claimed is:

1. A composition comprising

A) a polyolefin or polyolefin copolymer, and

B) as stabilizer against damage by light, oxygen and/or heat a compound of the formula I

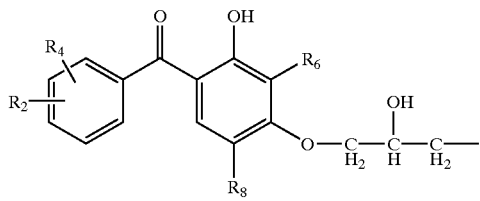

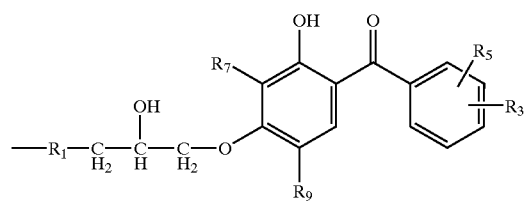

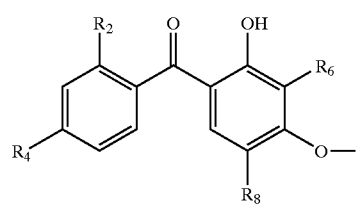

wherein $R_1$ is O or O—X—O;

$R_2$, $R_3$, $R_4$ and $R_5$ independently are hydrogen, halogen, $C_1$–$C_8$alkyl, $C_1$–$C_8$alkoxy, $SR_{10}$, $SO_2R_{10}$, phenyl, $CF_3$, $COOR_{11}$; and wherein $R_2$ and $R_3$ also may be OH;

$R_6$ and $R_7$ are H or $C_1$–$C_8$alkyl;

$R_8$ and $R_9$ are H, $C_1$–$C_8$alkyl or allyl;

$R_{10}$ is phenyl or $C_1$–$C_{12}$alkyl;

$R_{11}$ is $C_1$–$C_8$alkyl; $C_3$–$C_{50}$alkylene interrupted by O; or $R_{11}$ is cyclohexyl; benzyl; or allyl;

X is $C_2$–$C_{18}$alkylene; $C_3$–$C_{12}$hydroxyalkylene; or a group selected from those of the formulae

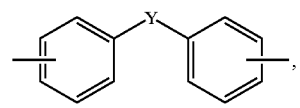

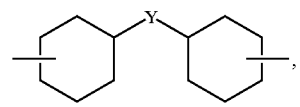

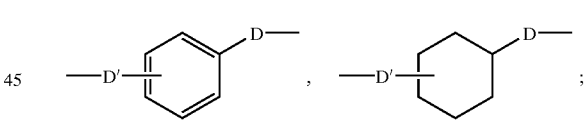

where D and D' independently are a direct bond or $C_1$–$C_3$alkylene; and

Y is O, S, $SO_2$, or $C_1$–$C_3$alkylene.

2. Composition of claim 1 wherein the compound of the formula I corresponds to the formula

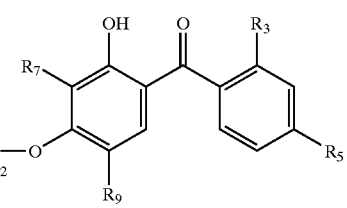

wherein $R_1$ is O or O—X—O;

$R_2$ and $R_3$ are hydrogen, Cl, $C_1$–$C_8$alkyl, $C_1$–$C_4$alkoxy, OH;

$R_4$ and $R_5$ are hydrogen, Cl, F, $C_1$–$C_8$alkyl, $C_1$–$C_4$alkoxy, $SR_{10}$, $SO_2R_{10}$, phenyl, $CF_3$, $COOR_{11}$;

X is $C_2$–$C_{12}$alkylene; phenylene, or a group selected from those of the formulae

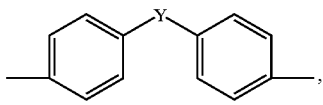

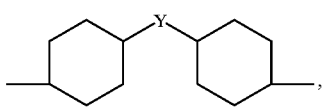

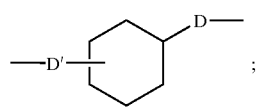

where D and D' independently are a direct bond or are methylene; and

Y is O, S, $SO_2$, or $C_1$–$C_3$alkylene.

3. Composition of claim 1 where in the compound of the formula I $R_1$ is O or O—X—O;

$R_2$ and $R_3$ are hydrogen, Cl, $C_1$–$C_8$alkyl, $C_1$–$C_4$alkoxy, OH;

$R_4$ and $R_5$ are hydrogen, Cl, $C_1$–$C_8$alkyl, $C_1$–$C_4$alkoxy, $SR_{10}$, $SO_2R_{10}$, phenyl, $CF_3$;

X is $C_2$–$C_{12}$alkylene; cyclohexylene, or a group selected from those of the formulae

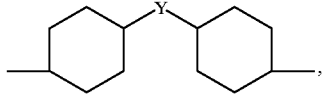

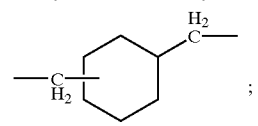

where Y is O, S, $SO_2$, methylene or —$C(CH_3)_2$—.

4. Composition of claim 1 where in the compound of the formula I $R_1$ is O—X—O, $R_2$ and $R_3$ are hydrogen, Cl;

$R_4$ and $R_5$ are hydrogen, Cl, $C_1$–$C_8$alkyl, $C_1$–$C_4$alkoxy, $SR_{10}$, $SO_2R_{10}$, phenyl, $CF_3$;

$R_6$, $R_7$, $R_8$ and $R_9$ are each H,

X is $C_2$–$C_{12}$alkylene; cyclohexylene, or a group selected from those of the formulae

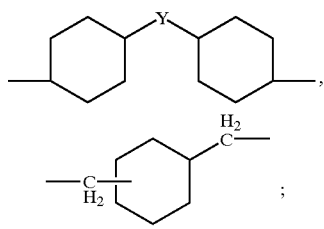

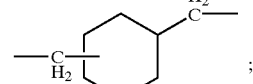

where Y is methylene or —$C(CH_3)_2$—.

5. Composition of claim 1 where in the compound of the formula I $R_2$ and $R_3$ are hydrogen;

$R_4$ and $R_5$ are hydrogen or Cl;

$R_6$, $R_7$, $R_8$ and $R_9$ each are hydrogen.

6. A polyolefin or polyolefin copolymer film, tape, fiber or fabric, manufactured from the composition of claim 1.

7. The method of using the tape or film of claim 6 for agriculture or food packaging.

8. A composition according to claim 1 comprising from 0.01 to 10% by weight, based on component A, of the stabilizer of component B.

9. A composition according to claim 1 comprising a further component selected from the group consisting of solvents, pigments, dyes, plasticizers, antioxidants, stabilizers, thixotropic agents, levelling assistants, further light stabilizers, metal passivators, phosphites and phosphonites.

10. A composition according to claim 9 comprising as further component a light stabilizer from the class of the sterically hindered amines.

11. A process for stabilizing a polyolefin or polyolefin copolymer against damage by light, oxygen and/or heat, which comprises adding to or applying to said material a compound of the formula I according to claim 1.

12. Compound of the formula Ia

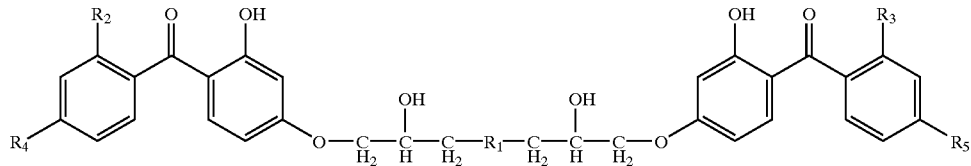

wherein $R_1$ is O or O—X—O;

$R_2$, $R_3$, $R_4$ and $R_5$ independently are hydrogen, halogen, $C_1$–$C_8$alkyl, $C_1$–$C_8$alkoxy, $SR_{10}$, $SO_2R_{10}$, phenyl, $CF_3$, $COOR_{11}$; and wherein $R_2$ and $R_3$ also may be OH;

$R_{10}$ is phenyl or $C_1$–$C_{12}$alkyl;

$R_{11}$ is $C_1$–$C_8$alkyl; $C_3$–$C_{50}$alkylene interrupted by O; cyclohexyl; benzyl; allyl;

X is $C_6$–$C_{18}$alkylene; $C_3$–$C_{12}$hydroxyalkylene; or a group selected from those of the formulae

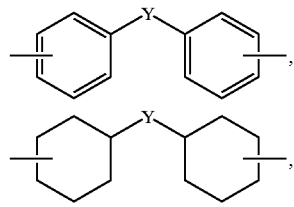

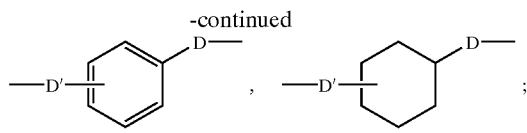

where D and D' independently are a direct bond or $C_1$–$C_3$alkylene; and

Y is O, S, $SO_2$.

13. A process for stabilizing an organic material against damage by light, oxygen and/or heat, which comprises adding to or applying to said material a compound of the formula Ia according to claim 12.

* * * * *